United States Patent [19]

Maffrand et al.

[11] 4,119,719
[45] Oct. 10, 1978

[54] PIPERAZINE COMPOUNDS

[75] Inventors: Jean-Pierre Maffrand; Jean-Marie Pereillo, both of Toulouse, France

[73] Assignee: Parcor, Paris, France

[21] Appl. No.: 833,291

[22] Filed: Sep. 14, 1977

Related U.S. Application Data

[62] Division of Ser. No. 664,943, Mar. 8, 1976, abandoned.

[30] Foreign Application Priority Data

Apr. 7, 1975 [FR] France .................. 75 10729

[51] Int. Cl.$^2$ .................. A61K 31/495; A61K 31/535
[52] U.S. Cl. .................. 424/250; 424/248.4
[58] Field of Search .................. 424/250

[56] References Cited

U.S. PATENT DOCUMENTS 3,005,821  10/1961  Hayao .................. 424/250
3,190,883   6/1965  Geschickter .................. 424/250

FOREIGN PATENT DOCUMENTS 3,708M  11/1965  France.

OTHER PUBLICATIONS

C. B. Pollard et al, J. Organic Chemistry, vol. 24, pp. 764–767 (1959).

Primary Examiner—Donald B. Moyer
Attorney, Agent, or Firm—Cushman, Darby & Cushman

[57] ABSTRACT

Piperazine compound of formula

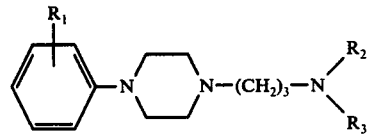

wherein $R_1$ is halogen, lower alkyl, lower alkoxy or trifluoromethyl, $R_2$ and $R_3$ form, together with the nitrogen atom to which they are attached a saturated heterocycle having n cyclic atoms, n being 4–8, have analgesic activity.

19 Claims, No Drawings

PIPERAZINE COMPOUNDS

This is a division of application Ser. No. 664,943 filed Mar. 8, 1976 now abandoned.

The present invention relates to new hypocholesterolaemic, anti-inflammatory and analgesic compositions. It also relates to new piperazine derivatives and a process for the preparation thereof.

The compositions according to the invention comprise, in addition to a pharmaceutically acceptable carrier, a compound of formula:

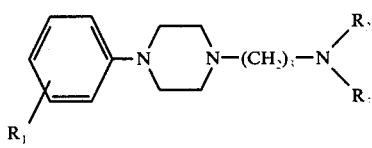

wherein $R_1$ represents a halogen, an alkyl, alkoxy or trifluoromethyl radical, $R_2$ is hydrogen and $R_3$ is an alkyl or cycloalkyl radical or else $R_2$ and $R_3$ form, together with the nitrogen atom to which they are attached, a saturated four-to eight-membered heterocycle which may comprise, as a second heteroatom, an oxygen or nitrogen atom.

In general, the alkyl and cycloalkyl radicals occurring in the above formula are lower radicals containing up to 12 carbon atoms. The alkyl radicals notably have up to 6 carbon atoms and the cycloalkyl radicals from 5 to 8 carbon atoms.

Preferably, the saturated heterocycle is a pyrrolidino, piperidino, morpholino or azetidino nucleus.

The composition according to the invention also includes the pharmaceutically acceptable addition salts with inorganic or organic acids and the quaternary ammonium derivatives of the compounds mentioned hereinbefore.

Some of the above-mentioned compounds were described in French Pat. No. 3708M for their activity, entirely different from that given here, of inhibiting the growth of protozoa, particularly those which cause sleeping sickness and schistosomiasis.

Some of the compounds are new. Some of these are compounds wherein $R_2$ and $R_3$ form a saturated heterocycle with four to eight cyclic atoms one of which is the nitrogen atom to which $R_2$ and $R_3$ are attached and the others are carbon atoms, while one of the latter may be replaced by a second oxygen or nitrogen heteroatom. Moreover, some of the new compounds are those wherein $R_2$ is hydrogen and $R_3$ is cycloalkyl.

A process for preparing the compounds of the invention consists in condensing a phenylpiperazine of formula:

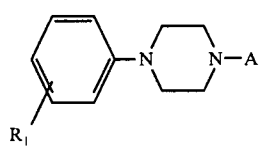

with a reagent B, wherein:
A is hydrogen when B is

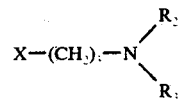

A is — $(CH_2)_3$ — X when B is

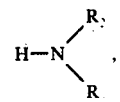

X being a halogen and, only when $R_2$ is hydrogen, A is — $(CH_2)_3NH_2$ when B is $R_4 = 0$, $R_4$ being the divalent radical obtained from $R_3$ by removing a hydrogen from the radical carbon atom, and in this latter case condensation is followed by a reduction of the imine obtained, by means of a reducing agent.

Thus, the three methods used in the process according to the invention are:

1. Condensation of 4-aryl-piperazines and 3-halogenopropylamines, according to the following reaction plan:

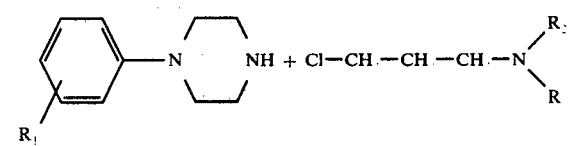

In this reaction, an organic solvent such as dimethylformamide or butanol can advantageously be used. It is necessary to work in the presence of a binding agent for hydrochloric acid formed during the reaction, such as for example potassium carbonate.

As catalyst, small quantities of potassium iodide can be used.

2. Condensing an amine and a 3-(4-aryl-1-piperazinyl)-1-chloro-propane according to the following reaction plan:

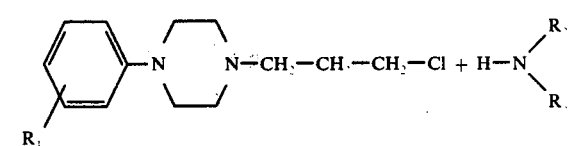

The reaction conditions are the same as in the previous method.

3. Condensing a 3-(4-aryl-1-piperazinyl)-propylamine and an aldehyde or ketone, then reducing the imine obtained by means of a reducing agent, such as sodium borohydride, according to the following reaction plan:

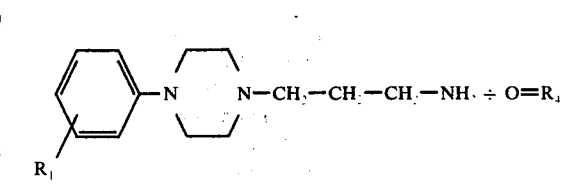

→

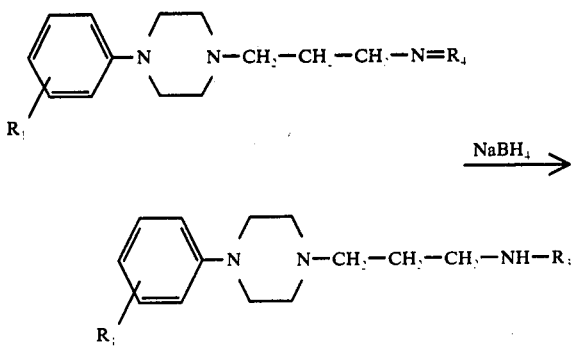

This method can only be used for the derivatives wherein the group

consists of —NH—R₃.

The process for preparing 4-aryl-piperazines, 3-(4-aryl-piperazino)-1-chloro-propane and 3-(4-aryl-piperazino)-propylamine, respectively, can be found in the following publications: P. C. Jain et al., J. Med. Chem. 1967, 10, 812; C. B. Pollard, W. M. Lauter and N. O. Nessle, J. Org. Chem, 1959, 24, 764: S. Hayao (Miles Lab.), U.S. Pat. No. 3,005,821.

The salts and quaternary ammonium derivatives are prepared by classic methods well known to the experts.

The following non-restrictive examples are given to illustrate the preparation of the compounds according to the invention.

EXAMPLE 1

Preparation of 1-(3-cyclohexylamino-propyl)-4-p-tolyl-piperazine

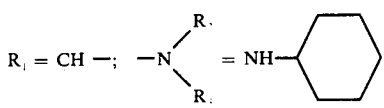

according to the 3rd method.

A solution containing 11.6 g of 1-(3-amino-propyl)-4-p-tolyl-piperazine, 5 g of cyclohexanone and 50 mg of p-toluenesulphonic acid in 100 ml of benzene is refluxed for 4 hours in an apparatus which enables the water formed during the reaction to be removed.

The reaction mixture is then evaporated and the residue is taken up in ethanol. 2.5 g of sodium borohydride are added to the solution obtained. After 2 hours' stirring at ambient temperarture, the mixture is evaporated and then taken up in dilute hydrochloric acid.

The solution obtained is washed with methylene chloride, then made alkaline by the addition of sodium carbonate. It is then extracted with chloroform. The organic fractions are combined and evaporated. The oil obtained is treated with a solution of hydrochloric acid in ethanol to form the hydrochloride of the desired product, which is filtered and recrystallized from ethanol. A white powder is thus obtained, with a melting point of 202° C, determined by the Koffler block (total yield 45%).

EXAMPLE 2

Preparation of 4-p-chlorophenyl-1-(3-piperidino-propyl)-piperazine

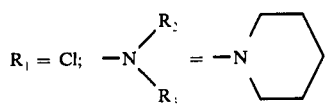

according to the 2nd method.

A mixture of 100 ml of n-butanol, 15 g of 4-p-chlorophenyl-1-(3-chloro-propyl)-piperazine, 5 g of piperidine, 7 g of potassium carbonate and 300 mg of potassium iodide is refluxed for one night. The solvent is then evaporated and the residue is taken up in chloroform and filtered. Then the filtrate is concentrated to obtain an oil, which is treated with a solution of hydrochloric acid in ethanol. The precipitated hydrochloride is filtered and again recrystallized from ethanol. A slightly pink powder is obtained with a melting point of 250° C, with decomposition, determined by the Koffler block (total yield 51%).

EXAMPLE 2(a)

Preparation of the derivative of example 2 (or derivative 2) by the 1st method.

A mixture of 100 ml of dimethyl formamide, 7.9 g of N-p-chlorophenyl piperazine, 8 g of 1-(3-chloro-propyl)-piperidine hydrochloride, 12 g of potassium carbonate and 600 mg of potassium iodide is heated to 30° C for 24 hours. After filtration, the hydrochloride of the desired product is precipitated by adding a solution of hydrochloric acid in ethanol. After filtration and recrystallization from ethanol, a slightly pink powder is obtained, with a melting point of 250° C (with decomposition) determined by the Koffler block (total yield 55%).

The following compounds were prepared by analogous methods:

EXAMPLE 3

1-(p-fluorophenyl)-4-(3-N-propylamino)propyl piperazine trihydrochloride -(R₁ = F; —NR₂R₃ = —NH—C₃H₇)—M.p. = 250° C (decomposition).

EXAMPLE 4

1-(3-n-propylamino propyl)-4-(m-trifluoro-methylphenyl)-piperazine dihydrochloride
(—R₁ = CF₃; —NR₂R₃ = —NH—C₃H₇)—M.p. = 250° C (decomposition).

EXAMPLE 5

1-(3-cyclohexylamino-propyl)-4-(p-chlorophenyl)-piperazine trihydrochloride
(—R₁ = Cl—; —NR₂R₃ =

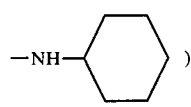

M.p. = 250° C.

EXAMPLE 6

4-(o-chlorophenyl)-1-(3-cyclohexylamino)-propyl-piperazine trihydrochloride
(—R$_1$ = Cl —; —NR$_2$R$_3$ =

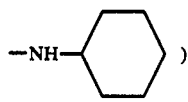

M.p. = 250° C.

EXAMPLE 7

1-(p-chlorophenyl)-4-(3-pyrrolidino-propyl)-piperazine dihydrochloride
(R$_1$ = Cl; —NR$_2$R$_3$ =

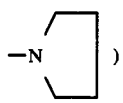

M.p. = 260° C (decomposition).

EXAMPLE 8

1-(p-methoxyphenyl)-4-(3-pyrrolidino-propyl)-piperazine trihydrochloride
(R$_1$ = —OCH$_3$; —NR$_2$R$_3$ =

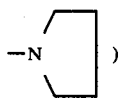

M.p. = 260° C (decomposition).

EXAMPLE 9

1-(p-chlorophenyl)-4-(1-morpholino-propyl)-piperazine dimaleate (—R$_1$ = Cl—; —NR$_2$R$_3$ =

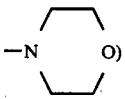

M.p. = 195° C.

The results of the toxicological and pharmacological tests reported hereinafter demonstrate the interesting activities of the derivatives according to the invention, particularly their hypocholesterolaemic, anti-inflammatory and analgesic properties.

The invention therefore also relates to a medicine with, in particular, hypocholesterolaemic, anti-inflammatory and analgesic activities, characterised in that it contains, as active principle, a compound according to the invention or a pharmaceutically acceptable acid addition salt or quaternary ammonium derivative of said derivative.

TOXICOLOGICAL STUDY

This demonstrated the low toxicity and good tolerance of the derivatives of the invention.

As a guide, the LD$_{50}$/24 hours/kg of body weight, determined by the method of Miller and Tainter, by intravenous route in mice is 25 mg for derivative no. 1, 53 mg for derivative no. 2, 89 mg for derivative no. 3, 57 mg for derivative no. 4, 41 mg for derivative no. 5, 62 mg for derivative no. 6, 66 mg for derivative no. 7, 74 mg for derivative no. 8 and 100 mg for derivative no. 9.

These experiments showed that, throughout the acute, chronic or retarded toxicity tests, the derivatives of the invention did not cause any local or general reaction or any disturbances in the biological checks carried out at regular intervals, in the test animals, or any anomalies in the macroscopic or microscopic examinations of the animals which were killed and on which autopsies were performed.

PHARMACOLOGICAL STUDY

1. Hypocholesterolaemic activity

This experiment demonstrated the clear hypocholesterolaemic and normolipaemic activity of the compounds of the invention. It was carried out using two methods.

(a) Test using propyl thiouracil (RANNEY and Coll., J. Pharmacol. Exper. Therap., 1963, 142, 132–136).

Propyl thiouracil administered to adult rats has the property of making them hypercholesterolaemic; the cholesterol level in the plasma rises by about 15% under these conditions. The tests are carried out on different batches of rats, the control batch being given only propyl thiouracil, while the other treated batches are also given the medicine according to the invention, orally, in a dosage of 10 mg/kg.

On the 11th day of the experiment, blood samples are taken and the free cholesterol and total cholesterol are estimated. It is observed that the cholesterol levels in the treated animals are significantly reduced, compared with the control animals.

The results obtained for certain derivatives are given in the following table:

|  | Free cholesterol g/l | Total cholesterol g/l |
| --- | --- | --- |
| Control | 0.21 | 0.82 |
| Derivative no. 2 | 0.13 | 0.62 |
| Derivative no. 5 | 0.16 | 0.55 |
| Derivative no. 6 | 0.15 | 0.53 |
| Derivative no. 7 | 0.12 | 0.50 |
| Derivative no. 9 | 0.13 | 0.57 |

These results are confirmed by the following test:

(b) This study was carried out on rabbits kept on a hypercholesterolaemic diet. The rabbits are divided into batches of 40 animals; the control batch (A) receives no treatment, whereas the treated batches are given the medicines according to the invention. Thus, derivative no. 1 is administered to the animals in batch B, derivative no. 5 to those in batch C and derivative no. 7 to those in batch D, by oral route, daily, in dosage of 10 mg/kg. On the first day of the experiments and then every 15 days, for a period of 75 days, biological tests are carried out on all the animals, whereby the various elements which indicate dyslipaemia are determined: total cholesterol (T), esterified cholesterol (E), free cholesterol (L), esterification ratio (E/T), Kunkel phenol test (K1), Kunkel phenol test (K2), Burstein test with dextrane (B) and serum lipids (LS).

At the end of the experiment, all the animals are killed and autopsies are performed on them; macroscopic examinations of their livers and aortas are then carried out, and the fatty infiltrations of the liver are marked, in size, from 0 to 3 and the aortic atheromatous lesions are marked, in intensity, from 0 to 4.

The results, representing the average values determined with each batch, are assembled in the following Tables:

| 1st Day Batches | T | E | L | E/T | K1 | K2 | B | LS |
|---|---|---|---|---|---|---|---|---|
| A | 0.54 | 0.28 | 0.26 | 0.51 | 7.9 | 12.3 | 10.3 | 2.06 |
| B | 0.55 | 0.28 | 0.27 | 0.50 | 8.2 | 13.7 | 11.1 | 1.95 |
| C | 0.57 | 0.28 | 0.29 | 0.49 | 8.1 | 12.6 | 10.9 | 2.1 |
| D | 0.52 | 0.27 | 0.25 | 0.51 | 8.1 | 13.2 | 10.6 | 1.98 |

| 30th Day Batches | T | E | L | E/T | K1 | K2 | B | LS |
|---|---|---|---|---|---|---|---|---|
| A | 2.29 | 1.46 | 0.83 | 0.63 | 21.6 | 31.5 | 26.6 | 3.89 |
| B | 1.47 | 0.92 | 0.55 | 0.62 | 18.6 | 25.4 | 21.2 | 2.91 |
| C | 1.45 | 0.91 | 0.54 | 0.62 | 18.8 | 25.0 | 21.1 | 2.85 |
| D | 1.51 | 0.96 | 0.55 | 0.63 | 18.5 | 25.2 | 21.2 | 2.88 |

| 75th Day Batches | T | E | L | E/T | K1 | K2 | B | LS |
|---|---|---|---|---|---|---|---|---|
| A | 3.67 | 2.27 | 1.40 | 0.61 | 43.3 | 66.5 | 51.8 | 5.19 |
| B | 2.92 | 1.80 | 1.12 | 0.66 | 33.1 | 41.9 | 35.8 | 4.03 |
| C | 2.92 | 1.78 | 1.14 | 0.60 | 32.8 | 41.8 | 35.9 | 4.1 |
| D | 2.95 | 1.83 | 1.12 | 0.62 | 32.9 | 50.0 | 35.6 | 3.97 |

| Batches | fatty infiltrations of the liver | aortic atheromatous lesions |
|---|---|---|
| A | 2.7 | 3.4 |
| B | 0.9 | 1.4 |
| C | 1.0 | 1.2 |
| D | 1.2 | 1.4 |

2. Anti-inflammatory activity

This activity was studied using two methods:

(a) Method using localised carrageenin-induced oedema

A 1% carrageenin solution (0.1 ml) is injected into the metatarsal flexors of the right hind paw of the rat at time 0. The animals in the treated batch are also given by oral route, 10 mg/kg of the test derivative, one hour before, then at the same time as the injection of the phlogogenic agent, then one hour and 2½ hours afterwards, respectively. The measurements taken with a Roch micrometer at time 0, then 1 hour, 2 hours, 3 hours and 5 hours after administration of the carrageenin make it possible to determine, as a function of time, the percentage anti-inflammatory activity compared with the control batch.

The results, with regard to derivatives nos. 3, 4 and 8, are given in the following table:

| | Percentage anti-inflammatory activity After | | | |
|---|---|---|---|---|
| | 1 hr | 2 hrs | 3 hrs | 5 hrs |
| derivative no. 3 | 31 | 44 | 47 | 49 |
| derivative no. 4 | 39 | 51 | 53 | 58 |
| derivative no. 8 | 37 | 48 | 50 | 54 |

(b) Method using generalised ovalbumin oedema

The rat is given a simultaneous intraperitoneal injection of 1 ml of ovalbumin and 0.5 ml of a 1% aqueous solution of Evans blue. Moreover, 50 mg of the test derivative are administered orally to the animals of the test batches one hour before and at the same time as the injection of ovalbumin. The intensity of the phenomenon thus induced is given a mark from 1 to 5, depending on the progression of the inflammatory syndrome. Thus, the average oedematous intensity and the percentage reduction in the oedematous reaction, compared with the control, are determined.

The results are given in the following table:

| | Percentage reduction in oedematous reaction | |
|---|---|---|
| | 2nd hour | 3rd hour |
| derivative no. 3 | 51 | 62 |
| derivative no. 4 | 49 | 61 |
| derivative no. 8 | 55 | 68 |

3. Analgesic activity

This activity was demonstrated using the method of KOSTER, ANDERSON AND DE BEER (Fed. Proceed., 18, 1959, 412, 1.626).

The intraperitoneal injection of a dilute solution of acetic acid causes, in mice, repeated characteristic stretching movements under the effect of the pain. The oral administration of a dosage of 50 mg/kg of the test derivative, thirty minutes before the injection of acetic acid, reduces the number of movements in the next thirty minutes. In this way, the average number of stretching movements and the percentage analgesia obtained, corresponding to the percentage reduction in the number of stretching movements, compared with the controls, are determined.

The results show that the average percentage of analgesia obtained is 65% for derivative no. 1, 72% for derivative no. 2, 61% for derivative no. 6 and 69% for derivative no. 7.

The toxicological and pharmacological studies reported above show that the compounds of the invention are well tolerated and have hypocholesterolaemic, anti-inflammatory and analgesic activities.

The medicine according to the invention may be presented, for oral administration, in the form of tablets, coated tablets, capsules, drops or syrup. For rectal administration, it may also be made up in the form of suppositories and, for parenteral administration, in the form of an injectable solution.

Each single dose advantageously contains from 0.010 g to 0.300 g of active principle, while the doses to be administered per day may vary from 0.010 g to 1 g of active principle.

Some pharmaceutical formulations of the medicine according to the invention are given hereinafter, as nonrestrictive examples:

| TABLETS | |
|---|---|
| 1. | |
| derivative no. 2 | 0.100 g |
| magnesium stearate | 0.005 g |
| talc | 0.005 g |
| dried fecula | 0.010 g |
| corn starch | 0.010 g |
| magnesium hydroxide | 0.010 g |

| COATED TABLETS | | |
|---|---|---|
| 2. | | |
| derivative no. 4 | 0.075 g | |
| fecula | 0.010 g | |
| | | Core |
| starch | 0.025 g | |

COATED TABLETS

| | |
|---|---|
| stearic acid | 0.005 g |
| lactose | 0.020 g |
| magnesium stearate | 0.010 g |
| polyvidone | 0.020 g |
| shellac | 0.005 g  Coating |
| gum arabic | 0.005 g |
| levilite | 0.002 g |
| white wax | 0.002 g |
| indigo blue | traces |
| sugar | q.s. for 1 coated tablet |

CAPSULES

3.

| | |
|---|---|
| derivative no. 5 | 0.150 g |
| magnesium stearate | 0.005 g |
| stearic acid | 0.005 g |
| talc | 0.003 g |

SYRUP

4.

| | |
|---|---|
| derivative no. 9 | 2.000 g |
| sweetened, flavoured excipient | q.s. for 100 ml |

SUPPOSITORIES

5.

| | |
|---|---|
| derivative no. 1 | 0.100 g |
| semi-synthetic triglycerides | q.s. for 1 suppository |

INJECTABLE SOLUTION

6.

| | |
|---|---|
| derivative no. 7 | 0.050 g |
| isotonic solution | q.s. for 3 ml |

By virtue of its hypocholesterolaemic, anti-inflammatory and analgesic properties, the medicine according to the invention may be usefully administered for therapeutic purposes.

It normalises the cholesterol and lipids levels in the blood by regularising their metabolism and thus effectively protects the organism from vascular complaints of atherosclerotic origin and their cardiac, cerebral or peripheral complications.

Thanks to its anti-inflammatory and analgesic activities, it enables inflammatory conditions to be combated effectively, whatever their etiology, and produces rapid and prolonged sedation of the pain which usually accompanies the inflammation.

What we claim:

1. A process for normalizing the cholesterol and lipid levels in the blood of a patient comprising administering to said patient daily from 0.01 to 0.300 g of a compound of the formula wherein $R_1$ is halogen, lower alkyl, lower alkoxy or trifluoromethyl, and $R_2$ and $R_3$ together with the nitrogen atom to which they are attached form a heterocycle selected from the group consisting of piperidino and pyrrolidino, or the pharmaceutically acceptable salts thereof.

2. The process of claim 1 wherein said compound is 4-p-chlorophenyl-1-(3-piperidino propyl) piperazine.

3. The process of claim 1 wherein $R_2$ and $R_3$ together form piperidino.

4. The process of claim 1 wherein $R_2$ and $R_3$ together form pyrrolidino.

5. A pharmaceutical composition comprising a pharmaceutically acceptable vehicle and a piperazine compound of the formula wherein $R_1$ is chlorine, alkyl having 1–6 carbon atoms or alkoxy having 1–6 carbon atoms and $R_2$ and $R_3$ together with the nitrogen atom to which they are attached form a heterocycle selected from the group consisting of piperidino and pyrrolidino, or a pharmaceutically acceptable salt thereof, said piperazine compound being present in an amount sufficient to provide hypocholesterolaemic, anti-inflammatory and analgesic activity.

6. The pharmaceutical composition of claim 5 wherein $R_2$ and $R_3$ together form piperidino.

7. The pharmaceutical composition of claim 5 wherein $R_2$ and $R_3$ together form pyrrolidino.

8. The pharmaceutical composition of claim 5 wherein said piperazine compound is 4-p-chlorophenyl-1-(3-piperidino propyl)piperazine.

9. A dosage unit of the pharmaceutical composition of claim 5 in an amount sufficient to provide 0.010 g to 0.300 g of said piperazine compound.

10. A process for normalizing the cholesterol and lipid levels in the blood of a human patient comprising administering to said patient sufficient dosage units of a pharmaceutical composition comprising a pharmaceutically acceptable vehicle and a piperazine compound of the formula wherein $R_1$ is chlorine, alkyl having 1–6 carbon atoms or alkoxy having 1–6 carbon atoms and $R_2$ and $R_3$ together with the nitrogen atom to which they are attached form a heterocycle selected from the group consisting of piperidino and pyrrolidino, or the pharmaceutically acceptable salts thereof.

11. The process of claim 10 wherein said compound is 4-p-chlorophenyl-1-(3-piperidino phenyl) piperazine.

12. The process of claim 10 wherein $R_2$ and $R_3$ together form piperidino.

13. The process of claim 10 wherein $R_2$ and $R_3$ together form pyrrolidino.

14. The process of claim 10 wherein said dosage units are administered at a rate sufficient to provide from 0.010 to 1 g of said piperazine compound per day.

15. A pharmaceutical composition comprising a pharmaceutically acceptable vehicle and a piperazine compound of the formula

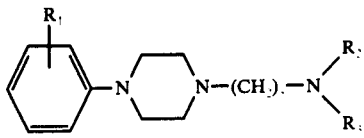

wherein
$R_1$ is selected from chlorine, fluorine, methyl, methoxy or trifluoromethyl, and $R_2$ and $R_3$ together with the nitrogen atom to which they are attached form a heterocycle selected from piperidino and pyrrolidino, or a pharmaceutically acceptable salt thereof, said piperazine compound being present in an amount effective to provide hypocholesterolaemic, anti-inflammatory and analgesic activity.

16. A dosage unit of the pharmaceutical composition of claim 15 in an amount sufficient to provide 0.010 g to 0.300 g of said piperazine compound.

17. The pharmaceutical composition of claim 15 wherein $R_2$ and $R_3$ together form piperidino.

18. The pharmaceutical composition of claim 15 wherein $R_2$ and $R_3$ together form pyrrolidono.

19. The pharmaceutical composition of claim 15 wherein said piperazine compound is 4-p-chlorophenyl-1-(3-piperidino propyl) piperazine.

* * * * *